United States Patent [19]

Mallard de la Varende et al.

[11] Patent Number: 5,756,358
[45] Date of Patent: *May 26, 1998

[54] COLORIMETRIC PROCESSES FOR THE DETERMINATION AND CONTROL OF THE PERACID CONTENT IN A SOLUTION, IN THE PRESENCE OF HYDROGEN PEROXIDE

[75] Inventors: Jean Mallard de la Varende, Boulogne; Pascal Crisinel, Versailles, both of France

[73] Assignee: L'Air Liquide, Societe Anonyme Pour L'Etude Et L'Exploitation Des Procedes Georges Claude, Paris, France

[*] Notice: The term of this patent shall not extend beyond the expiration date of Pat. No. 5,438,002.

[21] Appl. No.: 438,038

[22] Filed: May 8, 1995

Related U.S. Application Data

[62] Division of Ser. No. 768,279, filed as PCT/FR91/00203, Mar. 13, 1991, Pat. No. 5,438,002.

[30] Foreign Application Priority Data

Mar. 16, 1990 [FR] France .................... 90 03374

[51] Int. Cl.$^6$ .................................................. G01N 35/08
[52] U.S. Cl. ........................... 436/55; 436/129; 436/164
[58] Field of Search .................... 422/62, 74, 68.1, 422/82.09; 436/55, 104, 125, 126, 129, 164

[56] References Cited

U.S. PATENT DOCUMENTS

| | | | |
|---|---|---|---|
| 3,485,588 | 12/1969 | Fouts | 436/129 |
| 4,391,775 | 7/1983 | Huber et al. | 436/126 |
| 4,874,498 | 10/1989 | Freal-Saison | 204/400 |
| 4,900,682 | 2/1990 | Fischer et al. | 436/164 |
| 5,438,002 | 8/1995 | Mallard de la Varende et al. | 436/55 |

FOREIGN PATENT DOCUMENTS

| | | |
|---|---|---|
| 0 150 123 | 7/1985 | European Pat. Off. |
| 0 239 468 | 9/1987 | European Pat. Off. |
| 0 322 631 | 7/1989 | European Pat. Off. |

OTHER PUBLICATIONS

A.M. Siddiqi et al, *Chemist Analyst* 1955, 44, 52.
H. Thielemann *Textilreinigung* 1979, 26, 82–83.
T.C. Chou et al, *J. Chin. Inst. Chem. Eng.* 1986, 17, 215–222.
A.M. Siddiqi et al, *Chem. Abstr.* 1955, 49, 10123g.
R.D. Mair et al. *Anal Chem*, 1964, 36, 194–204.
O.D. Shapilov *USSR J. Anal Chem.* 1968, 23, 1624–1630.
O.D. Shapilov et al. *USSR J. Anal. Chem.* 1970, 25, 677–679.
D. Swern Ed. "Organic Peroxides" Wiley–Interscience, New York, 1970, 497–516.

(List continued on next page.)

*Primary Examiner*—Arlen Soderquist
*Attorney, Agent, or Firm*—Oliff & Berridge, PLC

[57] ABSTRACT

According to the invention, the content of peracid, in the presence of hydrogen peroxide, in a solution 2 in which the molar ratio between the concentration of hydrogen peroxide and the concentration of peracid is not higher than 100, is adjusted by means of a process according to which it is drawn by means of a pump 3 into the suction circuits of two pumps 5, 6 which operate at the same flow rate and may draw simultaneously a dilution and/or pH control liquid 9, pump 5 feeding the reference vat 7 of a two-beam photometer and pump 6 feeding its measuring vat 8, and the flow rates of the pumps 3, 5, 6 being adjusted so that the concentration of peracid in the measuring flow 10 is lower than about 100 ppm by weight, an excess of iodide 11 is added to the measuring flow 10 which exits from the pump 6 by means of a pump 13, a measuring unit 14 to which are connected the cells of the photometer compares the intensity of the iodine color formed in the measuring vat 8 to the reference in the reference vat 7 and transfers the difference to a regulator 16 which operates, if necessary, a pump 19 for the injection of the solution of peracid 20 into the solution 2.

14 Claims, 1 Drawing Sheet

OTHER PUBLICATIONS

J.P. Hawk et al. *Anal. Chem,* 1972, 44, 1315–1317.

M.A. Borisova et al. *USSR J. Anal. Chem,* 1974, 29, 522–523.

O.D. Shapilov et al. *USSR. J. Anal. Chem,* 1974, 29, 1417–1419.

R.E. Daly et al. *J. Pharm. Sci.* 1975, 64, 1999–2000.

J. Schneider et al. *Chem. Abstr,* 1977, 86, 11533c.

F. Di Furig et al. *Analyst* 1984, 109, 985–987.

M. Song *Chem. Abstr.* 1984, 101, 71365n.

T.C. Chou et al. *Chem. Abstr.* 1986, 105, 237583s.

D. M. Davies et al., "Determination of Peracids in the Presence of a Large Excess of Hydrogen Peroxide Using a Rapid and Convenient Spectrophotometric Method", Analyst, vol. 113, Sep. 1988, pp. 1477–1479.

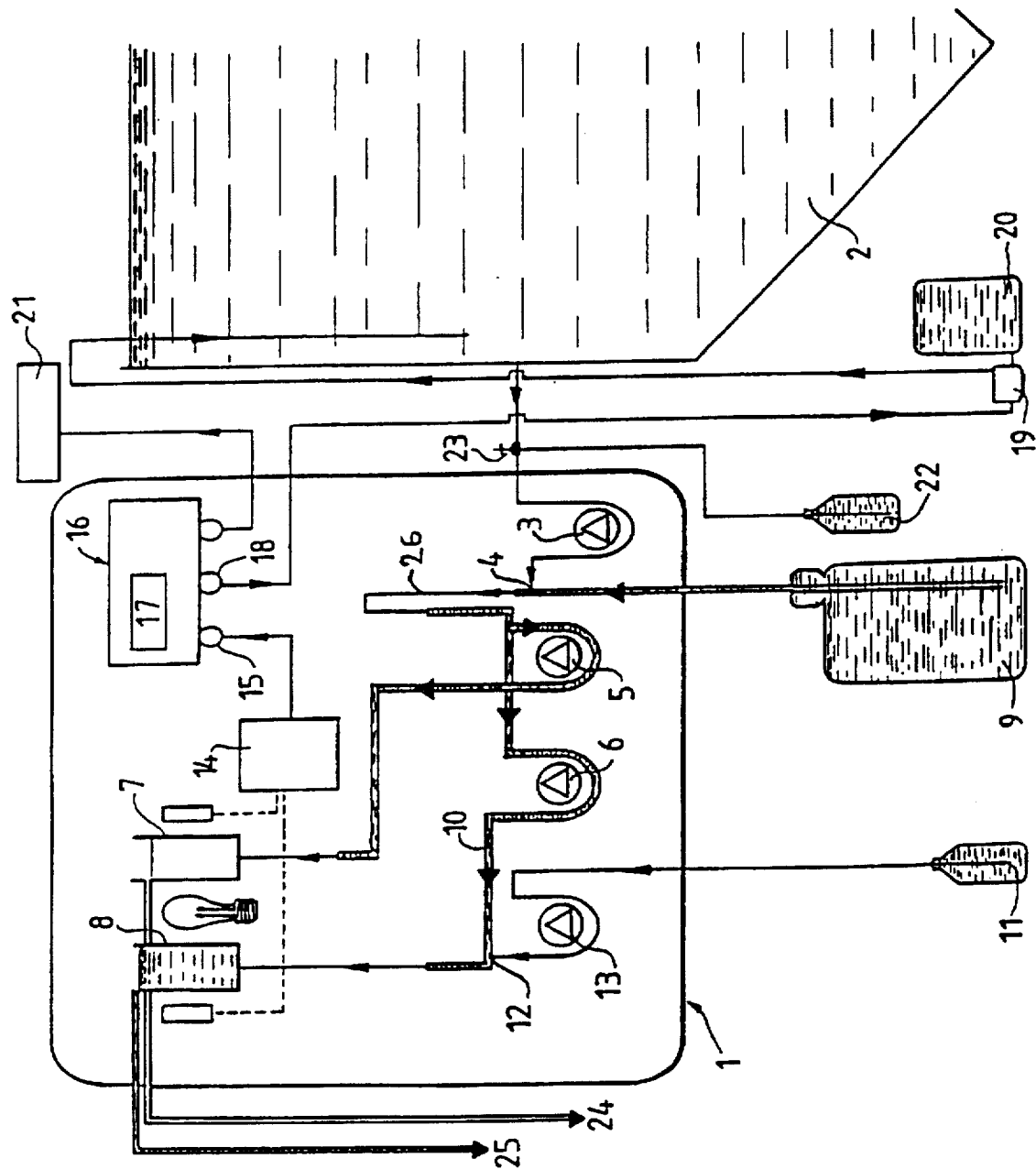

COLORIMETRIC PROCESSES FOR THE DETERMINATION AND CONTROL OF THE PERACID CONTENT IN A SOLUTION, IN THE PRESENCE OF HYDROGEN PEROXIDE

This is a Division of application Ser. No. 07/768,279 filed Oct. 1, 1991, now U.S. Pat. No. 5,438,002, which is a National Stage Application of PCT Application No. PCT/FR91/00203 filed Mar. 13, 1991.

The invention concerns the determination and control of the content of peracid in the presence of hydrogen peroxide in an oxidizing solution, for example a cleaning and/or disinfecting solution which may for example be used on an industrial scale.

For cleaning and/or disinfecting industrial installations, for example in dairies, there are generally used oxidizing solutions comprising a peracid, for example peracetic acid (PAA) and hydrogen peroxide, possibly in the presence of other compounds such as for example acetic acid and/or nitric acid.

These solutions are normally used in closed circuit, in a main network which is possibly part of the installation to be cleaned and/or disinfected.

They may be used in a system which includes recovery of the solution after use or in a system without recovery of the solution after use but in which the composition of the solution is verified, at more or less regular intervals, and is adjusted if necessary.

For example, when it is used for disinfecting, it is important to make sure that the composition of the solution which is utilized be such that it is active against the microorganisms to be destroyed. In this context, it is therefore recommended to control at least the concentration of the most active substance, such as the peracid, which more often is peracetic acid.

In the present industrial practice, the peracid is subject to a manual determination at the time of use. This determination enables one to determine the exact concentration of peracid (and also, if necessary, of hydrogen peroxide) but it is complicated and requires the assistance of specialized manpower, it cannot be automated and does not enable one to continuously adjust the amount of peracid.

Attempts have therefore been made to automate this determination by relying on a simple and inexpensive means which also enables one to adjust "in real time" the concentration of peracid, for example of peracetic acid.

To do this, a certain number of methods and devices which are described and commented briefly hereinafter have already been proposed.

Patent Application FR 2 595 837 (HENKEL FRANCE S.A.) proposes a solution which is essentially based on a potentiometric analysis in a measuring cell containing an electrode for measuring the redox potential of the oxydizing solution, and an electrode for measuring the pH of this solution. To obtain a significant reading, i.e. measuring points which are always on the same concentration/oxido-reduction potential curve within a zone in which variation is rapid, to prevent the polarization of the measuring electrode and to operate at constant pH, the proposed solution utilizes a secondary circuit enabling one to dilute the flow by means of an "adaptation solution". In the case of a solution containing hydrogen peroxide and a peracid, the analysis essentially indicates the concentration of hydrogen peroxide and not that of the truly active compound, namely peracid, for example peracetic acid.

On the other hand, other methods used, namely pH-metry and conductimetry give an indication with respect to the acidity of the medium but does not directly give information with respect to the evolution of the essential oxydizing agent, namely the peracid.

To analyze the disinfecting power of the solutions of the type in question, it has also been proposed to rely on colorimetry which enables one to distinguish between hydrogen peroxide and a peracid.

Thus, patent application EP 0 150 123 (INTEROX CHEMICALS LIMITED) describes a process for the analysis and control of the content of a peroxidized compound, such as peracetic acid, in the presence of hydrogen peroxide, by relying on calorimetric methods. This process is based on the fact that it is known that hydrogen peroxide reacts with colored reactants at room temperature, while peroxidized compounds, in particular peracetic acid, do not react significantly with these colored reagents but require heating to a temperature of for example 90° C. to completely develop a color. The process described therefore uses two measuring circuits one circuit being heated. The peroxidized compound concentration is obtained from the difference of intensity of the colors developed within these two circuits, one being due to hydrogen peroxide alone and the other, the hydrogen peroxide-peroxidized compound combination. This procedure, which implies the heating of one of the circuits, has the disadvantage of being complicated. Moreover and especially, it often gives an inaccurate reading of the peroxidized compound concentration in the industrial solutions normally used since the difference which is read has a relatively weak value and these solutions generally have a concentration of peroxidized compound, such as peracetic acid, which is much lower than the concentration of hydrogen peroxide.

It should also be noted that even though patent application EP 0 150 123 mentions on page 3, lines 28 to 32, the possible use of different calorimetric reagents for example iodides, it more particularly aims at the use of potassium and titanium oxalate and particularly sodium molybdate (see for example page 3, lines 27 and 37 and claim 4). In addition, it should be noted that the iodides could not be used in this process since, as will be seen later, they react very well with the peracids at room temperature, which on the contrary is not the case for hydrogen peroxide.

On the other hand, patent application EP 0 322 631 (MERCK PATENT GmbH) describes a process and a reagent for the determination of peracids, in particular peracetic acid, in the presence of hydrogen peroxide. The reagent used consists of a chromogen, an iodide and possibly a buffer. In this process, instead of measuring the coloring of the iodide formed during the oxido-reduction reaction, the coloring resulting from the chromogen is measured. As indicated on page 3, lines 6 to 8, the iodide concentration may be very low, for example on the order of one tenth of the chromogen concentration, since during the redox reaction the iodide is first consumed but is thereafter formed again; therefore it acts here exclusively as a catalyst. The concentration of peracid, for example of peracetic acid, is determined by means of a calibration curve. This document concerns a process for determination and an appropriate reagent therefor but does not describe nor suggest their use in the continuous control of the peracid content of a solution.

On the other hand, it is known that at room temperature, peracetic acid reacts nearly instantaneously with iodides to give iodine, while under these conditions, hydrogen peroxide reacts only very slowly, if at all. This reaction, characteristic of the peracids with the iodides, gave rise to different studies reported in the literature. Recently, D. Martin Davies and Michael E. Deary have proposed, in Analyst (London), September 1988, vol. 113, p 1477–1479, a spectrophotometric method for the determination of peracids in the presence of a large excess of hydrogen peroxide which utilizes this characteristic. This method, presented as being simple and fast, is in fact complicated since it implies, to determine each concentration of peracid, the formation of a curve of absorption as a function of time, after addition of the iodide to the sample, and the concentration in question is obtained by linear extrapolation at time t=0 when the iodide is added.

It has now been found according to the invention that it is possible to determine and control in a simple manner the amount of peracid, such as peracetic acid, in the presence of hydrogen peroxide, according to processes based on colorimetry and which do not require the use of two measuring circuits in which one is heated, with the disadvantages mentioned above with respect to the system described in patent application EP 0 150 123, by utilizing the different kinetic reaction of hydrogen peroxide and peracids with the iodides mentioned above, without having to establish a specific curve for each determination, as in the case of the process described in Analyst and commented above.

According to the invention, it has indeed been established that it is possible to obtain, by calorimetric analysis at room temperature, of mixtures of hydrogen peroxide and peracid in which the molar ratio between the concentration of hydrogen peroxide and the concentration of peracid does not exceed about 100, a linear response of the coloring which is read as a function of the concentration of peracid, after addition of an excess of iodide, for a given reaction time. The reading of the concentration can then be made directly on a calibration curve prepared from two points, or on an appropriate apparatus, also calibrated starting from two "points".

According to one to aspect, it is an object of the invention is to provide a process or the calorimetric determination, by formation of iodine from an excess of iodide, of the amount of peracid in and an at least partially aqueous solution, in which the molar ratio between the concentration of hydrogen peroxide and the concentration of peracid does not exceed about 100, characterized in that:

the determination is made at about room temperature, the pH of the solution at the time of its determination is adjusted at a value lower than or equal to 6.5, the time gap between the addition of excess iodide and the reading of the iodine color developed, is predetermined, and the determination is carried out from the value which has been read, by means of a calibrating system, such as with two points.

This process is particularly applicable in the case where the peracid is peracetic acid which is often currently used for the disinfection of industrial installations, for example in dairy.

The possibility of making the determination, i.e. at a temperature of between a about 5° to 40° C., has a noted advantage as compared to the prior art such as illustrated for example in patent application EP 0 150 123. This being the case, the temperature, if possible, should not exceed 50° C., since then the measurement would be less accurate, the hydrogen peroxide present in the medium then starting to react in a non negligible manner with the iodide to produce iodine.

It is well known that the oxidation of an iodide into iodine may only take place in an acid medium. In this connection, it has been observed that satisfactory results will only be obtained if the pH, during the determination, is lower than or equal to 6.5.

Satisfactory results are also obtained in very acid solutions (pH=1) but this generally presents no interest since the solutions for which determination is normally made have higher pH, and on the other hand, in very acidic medium, the results are less accurate since the hydrogen peroxide then starts to react in a relatively significant manner.

It has been observed that the best results are obtained for pH values between 5 and 6.3; this range is therefore preferred.

If necessary, the adjustment of the pH is carried out by addition of an acid such as for example phosphoric acid or by means of a buffer, such as a phosphate buffer.

The iodide used may be selected, for example, from the alkali metal iodides and ammonium iodide, however potassium iodide is preferred.

The time gap between the addition of excess iodide and the reading of the iodine color which has developed should always be the same among a series of given measurements, including when calibration is made.

This time gap may vary within a large range. It may for example be of the order of 2 to 2 and a half minutes. Preferably, however, it should be shorter than 1 minute.

On the other hand, to give accurate measurements, it is desirable that the iodine color formed not be too intense. To do this, it is recommended that the weight concentration of the peracid in the medium during the determination be lower than 100 ppm (parts per million), preferably lower than 50 ppm.

If necessary, the sample is diluted when the determination is made. The diluting liquid used (such as tap water or distilled water) may also contain, if necessary, the acid or the buffer to be used for adjusting the pH.

The range of wavelengths used for the measurement, generally between 370 and 500 nm, essentially depends on the concentration of peracid in the medium during the determination.

The two point calibration system includes the straight line representing the variations of the optical density which is read as a function of the concentration in peracid, for example peracetic acid.

The two point calibration may be obtained by means of a solution having a known concentration of peracid, without addition of iodide for value 0 and with addition of iodide for the value read corresponding to said known concentration.

According to another aspect an object of the invention to provide a calorimetric process for the control of the amount of peracid, in the presence of hydrogen peroxide in an at least partly aqueous solution, in which the molar ratio between the concentration of hydrogen peroxide and the concentration of peracid does not exceed about 100, characterized in that:

the solution to be controlled is drawn by means of a suction means, for example a peristaltic pump, into the drawing circuits of a second and third suction means, for example peristaltic pumps, operating under the same flow rate and which can simultaneously draw a dilution and/or pH control liquid, the second suction means feeding the reference vat of a two-beam photometer and the third suction means feeding the measuring vat of said photometer, the flow rates of the three suction means are adjusted so that the concentration of peracid in the measuring flow drawn by said second and third suction means being lower than about 100 ppm (parts per million) by weight, an excess of iodide is added to the measuring flow which exits from the third suction means, by means of a fourth suction means, for example a peristaltic pump, the cells of the photometer are connected to a measuring unit which compares the intensity of the iodine color formed in the measuring vat by reference to the reference vat and transfers the difference to a regulator, which regulator operates, if necessary, a pump for the injection of a solution of peracid into the medium to be controlled.

The dilution reagent is advantageously made of tap water or possibly distilled water, to which, if necessary, there is added a pH regulator such as for example phosphoric acid or a phosphate buffer.

The iodide used may be selected such as from the alkali metal iodides and ammonium iodide, however potassium iodide is preferred.

The iodide solution is relatively concentrated in order not to substantially modify the dilution of the flow which penetrates into the measuring vat, as compared to that of the flow which enters into the reference vat. Advantageously, a solution of potassium iodide at a concentration of 1 to 3 weight % may be used.

Advantageously, the measuring unit transforms the difference of intensity into a potential difference, for example in the range of 0 to 2 V, or into a current intensity, for example within the range of 4–20 mA.

Advantageously, the regulator includes a displaying means, for example with liquid crystals, to display the instantaneous concentration of peracid.

Still advantageously, the regulator is connected to a printer which reproduces the variations of concentration.

The added solution of peracid may comprise an aqueous solution containing for example 0.05 to 5% by weight of peracid, such as an aqueous solution containing 2.5% by weight of peracetic acid, when the latter constitutes the peracid whose concentration should be controlled.

According to a preferred embodiment, the dilution and/or pH control solution which is injected into the measuring flow is intimately mixed with the solution to be adjusted, through a mixing means located between its meeting point with the liquid to be analyzed and before the second and third suction means and which may advantageously consist of a constriction followed by a widening of the tube in which the mixture flows.

Calibration of the regulator is carried out by means of a calibrated or standard solution of known peracid concentration. Advantageously, the installation used includes a three way valve, mounted ahead of the first injection means and which enables the to introduce the standard solution or the solution to be adjusted, into the measuring circuit.

DESCRIPTION OF THE SINGLE FIGURE

The annexed single figure is a schematic representation of a mode of operation of the control process according to the invention utilizing a device 1 for controlling the content of peracetic acid in the presence of hydrogen peroxide in a cleaning and/or disinfecting solution 2, such as for the cleaning in situ (N.E.P.) in a dairy.

The device 1 may consist of the apparatus manufactured by TECAN (Switzerland) and sold in France by IMATEK under the designation "Compact 150" to control the chlorine concentration in public swimming pools with however certain modifications, namely for example the replacement of the original colorimetric filter by means of a filter having a pass band of 430–470 nm, or 450–500 nm, on the one hand, and on the other hand the addition of a system of dilution and/or pH control (dilution and/or pH control liquid 9, peristaltic pump 3).

A peristaltic pump 3 draws the solution to be analyzed and injects same at 4 in the suction circuit of two peristaltic pumps 5 and 6 which reed at the same flow rate two vats of a two-beam photometer, namely reference vat 7 and measuring vat 8, respectively. These two peristaltic pumps 5 and 6 have identical characteristics and draw if necessary, in addition to the liquid to be analyzed 2 supplied by the peristaltic pump 3, dilution and/or pH control liquid 9 consisting of tap water or distilled water, possibly containing a buffer to adjust the pH of the measuring flow 10 to a value lower than 6.5 thus permitting a complete reaction of the peracetic acid contained in the liquid to be analyzed 2 with excess iodide 11 injected at 12 of the measuring flow, by means of the peristaltic pump 13. The flow rates of the peristaltic pumps 3, 5 and 6 are adjusted so that the concentration of peracetic acid of the measuring flow at 10 should be lower than 100 ppm. It is advantageous to introduce a mixer 26, between the point of injection 4 of the solution to be analyzed and the peristaltic pump 5 to homogenize the mixture of liquid to be analyzed 2 and dilution liquid 9. This mixer may for example comprise a restriction followed by a widening of the feeding tube as shown, which renders the circulating flow sufficiently turbulent to homogenize same. As already indicated above, a fourth peristaltic pump 13 injects into the measured flow at 12 a known quantity of iodide 11, such as potassium iodide, in excess.

After a certain delay which is directly dependent on the length of the trajectory between the point of injection 12 of the iodide 11 and the analysis vat 8, on the one hand, and the duration of homogenization in the analyzing vat 8, on the other hand, the intensity of the iodine color formed (yellow to red) in the analyzing vat 8 is measured and compared to the reference in vat 7. The difference is transformed into current (4–20 mA) in the measuring unit 14, then this current is transmitted at 15 to a regulator 16 where it is transformed into information on a liquid crystal display 17. This regulator transmits at 18 the guiding information to the pump 19 which injects if necessary additional peracetic acid 20 into the cleaning and/or disinfecting product 2.

The informations supplied to the regulator 16 may be transmitted to a printer 21.

The regulator 16 may be calibrated on the basis of two measuring points, namely zero and the concentration of a standard or caliber 22. Indeed, the concentration of peracetic acid in the measuring flow 10 is adjusted so that the intensity of the iodine color formed is proportional to the concentration of peracetic acid. Zero is obtained by removing the addition of iodide 11. The standard or caliber 22 is obtained by manual dilution of the solution of peracetic acid 20. The introduction of this standard or caliber 22 is carried out by means of three way valve 23. Pump 3 draws either the standard 22 when the calibration is carried out, or the solution to be analyzed 2 when the concentration of peracetic acid is determined and/or adjusted.

In this connection, it should be noted that in certain particular cases (dilution and pH control not required), pump 3 and dilution and/or pH control reagent 9 may be omitted. In this case, the pumps 5 and 6 directly draw either the solution to be analyzed 2, or the standard 22.

By means of this calibration, the value read on the liquid crystal display 17 during the measurement is the concentration of peracetic acid in solution 2.

It is thus possible to program the desired value of the concentration and the proportional range of adjustment. The operation is then carried out with a pump 19 for adding a solution of peracetic acid 20 which is controlled either "completely or not at all" (the pump 19 starts to operate at any value below the control point), or by contact-relay, or starting from information called 4–20 mA, for example.

These last two solutions are more satisfactory since the inertia of the measuring system is 5 to 10 minutes when the proportional range of control modifies the information sent to the pump 19.

On the other hand, to be more secured, the regulator 16 may have two alarm limits "high-low" who are to be defined by the user which is thus advised whether one of these limits is exceeded more than for a certain time, which is also to be defined.

The liquids of the reference 7 and analyzing 3 vats are thrown at 24 and 25, respectively.

EXAMPLES

The device described above has been used to monitor the concentration of peracetic acid of a diluted cleaning solution in place (N.E.P.) in a dairy in the presence of hydrogen peroxide. The aim was to maintain this concentration at a level suitable during one week.

Such a solution is sent into ducts of the installation of the dairy to disinfect same after an acid and/or basic cleaning. A portion of the peracetic acid is consumed or hydrolyzed during this operation of disinfection. It is therefore recommended to proceed with readjustments of the concentration of this acid as time goes. The control process according to the invention enables one to maintain this solution always ready to be used, without manual intervention.

A cycle of one week was realized in the laboratory in a 30 liter vat containing a disinfection solution, with adjustment to the initial desired titer and monitored during the entire week. Because, for different reasons, as time goes a decrease of the total volume of the solution is noted, an addition of 10% water was carried out 3 times during the week to off-set for a more important loss of titer than that which is uniquely due to hydrolysis.

The product tested essentially consisted of 25,000 ppm (by weight) of peracetic acid, 190,000 ppm (by weight) of hydrogen peroxide, in the presence of acetic acid and nitric acid. It was used here under the usual conditions of use in a dairy, namely as a 0.4% solution, which corresponded to a concentration of 100 ppm (by Weight) of peracetic acid and 760 ppm (by weight) of hydrogen peroxide in the initial mixture.

For the measurements, the flows of pumps 3, 5 and 6 were adjusted so that the sample to be analyzed 2 was diluted at ½th with dilution water 9 whose pH was between 5 and 6.5. This pH was adjusted by means of phosphoric acid.

In a first experiment, the filter used had a pass band of 430–470 nm.

Calibration was carried out with the same solution at 0.5% by weight and was not modified during the week of testing. The liquid crystal display during the calibration indicated 0.50.

The results obtained with the solution being studied are given in table I which follows:

In this table:

"display read" represents the values read on the apparatus;
"expected display" represents the values obtained by manual determinations of peracetic acid (PAA) in the N.E.P. solution.

TABLE I

| Days | Display read | Expected display |
|---|---|---|
| 0 | 0.46 | 0.46 |
| 2 | 0.42 | 0.42 |
| 4 | 0.40 | 0.41 |
| 7 | 0.43 | 0.39 |

Conclusion: the relative error between the display read and the expected display is a maximum of 10%, which is also the limit of error of the manual proportioning and is completely acceptable for an industrial disinfection.

A second experiment was carried out by utilizing the same apparatus, except that a filter having a pass band of 460 to 500 nm and the same solution as before, except at 0.7% instead of 0.4%, were used. Calibration was again carried out with the same solution at a concentration of 0.5%.

The results obtained in this second experiment are given in table II which follows:

TABLE II

| Days | Display read | Expected display |
|---|---|---|
| 0 | 0.71 | 0.71 |
| 1 | 0.70 | 0.69 |
| 2 | 0.70 | 0.68 |
| 3 | 0.72 | 0.71 |
| 4 | 0.70 | 0.67 |
| 7 | 0.72 | 0.70 |

Interference tests with milk have shown that up to a concentration of 0.2% of whole milk in the solution to be analyzed, no disturbance was observed on the apparatus, while for this concentration the turbidity was 200 units of formazine turbidity (FTU), which corresponds to a relatively important turbidity.

We claim:

1. Colorimetric process for a determination, by formation of iodine from an excess iodide, of a content of peracid in the presence of hydrogen peroxide in an at least partly aqueous solution, in which a molar ratio between a concentration of hydrogen peroxide and a concentration of peracid does not exceed about comprising the steps of:
   adjusting pH of the solution at a time of the determination to a value from 5 to 6.5;
   reading a value of an intensity of an iodine color developed after a predetermined time gap following an addition of excess iodide; and
   determining the content of peracid from the value read, by means of a system of calibration, wherein the determination is made at a temperature ranging from 5° C. to 50° C., wherein the concentration of peracid during the determination is lower than about 100 ppm by weight.

2. Process according to claim 1, wherein the peracid is peracetic acid.

3. Process according to claim 1, wherein the pH at at least one of a time of determination and a time of adjustment is adjusted at a value between 5 and 6.3.

4. Process according to claim 1, wherein the pH is adjusted by means of phosphoric acid or a phosphate buffer.

5. Processing according to claim 1, wherein the iodide is potassium iodide.

6. Process according to claim 1, wherein a time gap between the addition of excess iodide and the reading of the iodine color developed is about 2 to 2 and one half minutes.

7. Process according to claim 1, wherein the concentration of peracid during the determination is lower than 50 ppm (parts per million) by weight.

8. Process according to claim 1, wherein the system of calibration comprising at least two calorimetric measurements corresponding to at least two peracid contents.

9. Process according to claim 1, wherein the system of calibration is a 2 point calibration system.

10. Process according to claim 1, wherein the time gap is less than 1 minute.

11. Process according to claim 1, wherein said temperature ranges from 5° C. to 40° C.

12. Process for determination and adjustment to a desired concentration of a content of peracid in the presence of hydrogen peroxide in an at least partly aqueous solution, in which a molar ratio between a concentration of hydrogen peroxide and a concentration of peracid does not exceed about 100, comprising the steps of:

adding an excess of iodide to said solution;

adjusting pH of the solution at the time of the determination to a value from 5 to 6.5;

reading a value of an intensity of an iodine color developed after a predetermined time gap following the addition of excess iodide;

determining the content of peracid from the value read, by means of a system of calibration, the determination being made at a temperature ranging from 5° C. to 50° C., wherein the concentration of peracid during the determination is lower than about 100 ppm by weight; and adding peracid to said solution to adjust the peracid content to a desired concentration.

13. Process according to claim 12, wherein the peracid is peracetic acid.

14. Process according to claim 12, wherein said concentration of peracid during the determination is lower than about 50 ppm by weight.

* * * * *